(12) United States Patent
Hebrank et al.

(10) Patent No.: US 6,224,316 B1
(45) Date of Patent: May 1, 2001

(54) EGG REMOVAL APPARATUS

(75) Inventors: John H. Hebrank, Durham; Daniel T. DePauw, Raleigh, both of NC (US)

(73) Assignee: Embrex, Inc., Research Triangle Park, NC (US)

( * ) Notice: Subject to any disclaimer, the term of this patent is extended or adjusted under 35 U.S.C. 154(b) by 0 days.

(21) Appl. No.: 09/565,895

(22) Filed: May 5, 2000

Related U.S. Application Data

(62) Division of application No. 09/271,520, filed on Mar. 18, 1999.

(51) Int. Cl.⁷ .............................. B65B 23/02; B65B 23/08
(52) U.S. Cl. ........................... 414/404; 414/403; 414/737; 209/644; 294/64.1
(58) Field of Search .................... 414/403, 737, 414/404; 209/644; 294/64.1

(56) References Cited

U.S. PATENT DOCUMENTS

| | | | |
|---|---|---|---|
| 3,773,172 | 11/1973 | McClure et al. | 209/73 |
| 3,910,416 | 10/1975 | Payne | 209/74 |
| 3,928,184 | * 12/1975 | Anschutz | 209/644 X |
| 4,091,931 | 5/1978 | Button et al. | 209/73 |
| 4,355,936 | * 10/1982 | Thomas et al. | 414/796.2 |
| 4,671,652 | 6/1987 | van Asselt et al. | 356/66 |
| 4,703,925 | * 11/1987 | Jelinek et al. | |
| 4,768,919 | * 9/1988 | Borgman et al. | 414/752 |
| 4,901,861 | 2/1990 | Cicchelli | 209/539 |
| 4,903,635 | 2/1990 | Hebrank | 119/1 |
| 5,699,751 | 12/1997 | Phelps et al. | 119/6.8 |
| 5,745,228 | 4/1998 | Hebrank et al. | 356/53 |

FOREIGN PATENT DOCUMENTS

8906797 * 7/1989 (WO) .

* cited by examiner

*Primary Examiner*—Steven A. Bratlie
(74) *Attorney, Agent, or Firm*—Myers Bigel Sibley & Sajovec

(57) ABSTRACT

An egg removal apparatus includes a frame and a manifold removably secured to the frame. The frame is movable from a first location overlying an egg flat to a second location overlying an area adjacent the egg flat. When the frame is in the first location, eggs from an egg flat are picked up under vacuum via a plurality of flexible cups. When the frame is in the second position, the eggs are released from the plurality of flexible cups. The removable manifold can be quickly and easily removed from a supporting frame and cleaned as a unit.

24 Claims, 14 Drawing Sheets

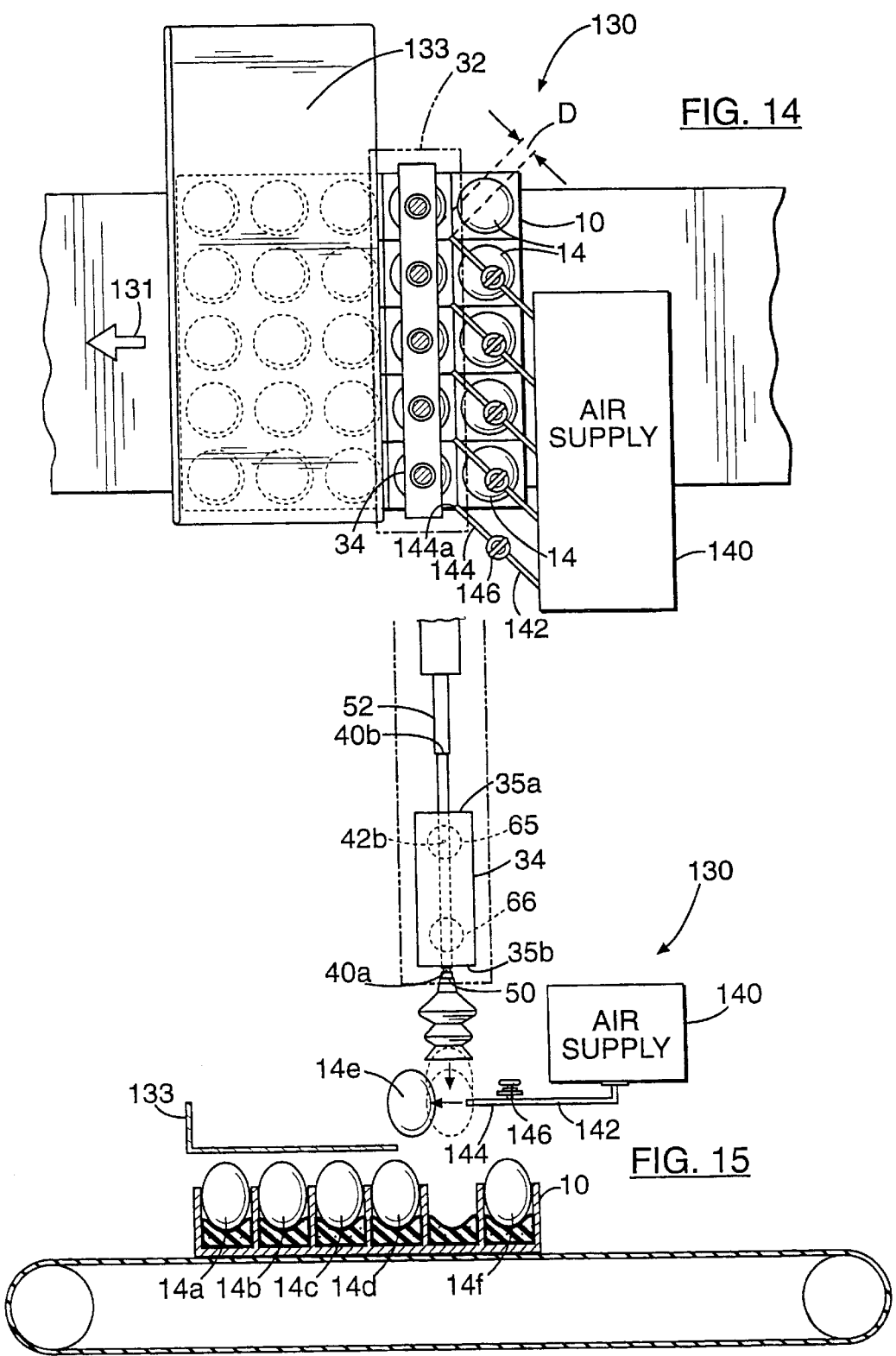

EGG REMOVAL APPARATUS

This application is a Division of Ser. No. 09/271,520 filed Mar. 18, 1999.

FIELD OF THE INVENTION

The present invention relates generally to eggs and, more particularly, to methods and apparatus for handling eggs.

BACKGROUND OF THE INVENTION

Advances in poultry embryology have made possible the addition of various materials to the embryo or to the environment around the embryo within an avian egg for the purpose of encouraging beneficial effects in the subsequently hatched chick. Such beneficial effects include increased growth, prevention of disease, increasing the percentage hatch of multiple incubated eggs, and otherwise improving physical characteristics of hatched poultry. Additionally, certain types of vaccinations which could previously only be carried out upon either recently hatched or fully mature poultry can now be successful in the embryonated chick.

In ovo vaccination techniques can increase vaccination efficiency and can reduce stress on young chicks caused by injection. Conventional in ovo inoculating devices typically inject all eggs contained within an egg flat. An exemplary in ovo inoculating device that injects all eggs contained within an egg flat is described in U.S. Pat. No. 4,903,635 to Hebrank.

Unfortunately, it may not be desirable to administer vaccinations into every egg contained within an egg flat. For example, "clear" eggs are eggs that do not contain an embryo and, thus, may not subsequently hatch as a chick. The administration of vaccinations into clear eggs generally serves no purpose and may be considered wasteful. In addition, mold may grow in clear eggs that have been injected, thus increasing the risk of exposing other eggs and hatched chicks to undesirable contamination. Furthermore, injected clear eggs may increase the risk of contamination resulting from albumin leaking therefrom. Accordingly, it is desirable to quickly identify and remove clear eggs from an egg flat prior to the in ovo administration of vaccinations via automatic inoculating devices.

It may also be desirable to selectively remove certain eggs from an egg flat. For example, it may be desirable to remove certain types of eggs, such as all male eggs, all rotten eggs, and the like. As another example, it may be desirable to remove all live eggs in order to move them to another egg flat or injection apparatus.

A conventional device 5 for removing eggs from an egg flat is illustrated in FIG. 1. A plurality of suction devices 7 are configured to engage the upwardly facing portions of a respective plurality of individual eggs 14 within an egg flat 10, and hold the eggs by suction while carrying them to a receptacle 11. During removal of eggs, it is conventionally expected that some breakage of eggs will occur. Accordingly, it is conventionally expected that egg removal devices will become contaminated with the contents of broken eggs.

Unfortunately, conventional egg removal devices, such as that illustrated in FIG. 1, are complex and bulky devices that can be difficult and time consuming to clean. Maintaining conventional egg removal devices in sanitary condition, thus, can be expensive and labor intensive. Accordingly, it would be desirable to provide egg removal devices that can be quickly and easily cleaned.

SUMMARY OF THE INVENTION

It is, therefore, an object of the present invention to provide egg removal devices that can be quickly and easily cleaned.

It is another object of the present invention to facilitate the selective removal of eggs from an egg flat.

These and other objects of the present invention can be provided by an egg removal apparatus that includes a frame and a manifold removably secured to the frame. The frame is movable from a first location overlying an egg flat to a second location overlying an area adjacent the egg flat. When the frame is in the first location, eggs from an egg flat are picked up under vacuum via a plurality of flexible cups. When the frame is in the second position, the eggs are released from the plurality of flexible cups. The manifold includes opposite upper and lower surfaces, a plurality of internal passageways, and a plurality of plunger bores extending from the upper surface to the lower surface. Each plunger bore is in communication with one of the internal passageways.

An elongated plunger is supported for reciprocal movement in each plunger bore. Each plunger is configured to be moved from an initial first position to a second position. An internal bore extends axially within each plunger from a lower end to a port in a medial portion thereof. Accordingly, when a plunger is moved to the second position, the port in the medial portion of the plunger is in communication with a respective manifold internal passageway. An actuator is mounted to the frame above each respective plunger upper end and serves as means for moving a respective plunger from the first position to the second position. A spring serves as means for returning a plunger from the second position to the first position.

A flexible cup is secured to the lower end of each plunger and is in fluid communication with the internal bore of the respective plunger. When a plunger is moved to the second position, vacuum is provided within each flexible cup via a respective plunger internal bore. Thus, when a plunger is in the second position, a flexible cup attached thereto can engage and retain an egg via suction in seated relation therewith. To release an egg from a flexible cup, vacuum within the flexible cup is destroyed, either by moving the respective plunger to the first position or by introducing positive air pressure into the manifold internal passageways while the plunger is in the second position.

According to another embodiment of the present invention, a removable manifold may be provided with first and second sets of internal passageways. Positive air pressure is maintained within the first set of internal passageways and vacuum is maintained within the second set of internal passageways. A plurality of plunger bores extend through the manifold. Each plunger bore is in communication with one of the first and second sets of internal passageways.

An elongated plunger is supported for reciprocal movement in each plunger bore. Each plunger is configured to be moved from an initial first position to a second position. An internal bore extends axially within each plunger from a lower end to a port in a medial portion thereof. When a plunger is in the first position, the second port of the plunger is in communication with a respective one of the first set of internal passageways. When the plunger is in the second position, the second port is in communication with a respective one of the second set of internal passageways.

Accordingly, when a plunger is moved to the second position, a flexible cup secured to the lower end of the plunger can retain an egg in seated relation therewith because of the vacuum provided to the flexible cup via the internal bore. To release the egg from the flexible cup, the plunger is moved to the first position so that positive air pressure is introduced into the flexible cup via the internal bore, which is now in communication with one of the internal passageways of the first set.

According to another embodiment of the present invention, a manifold removably secured to a movable frame includes opposite upper and lower surfaces, a plurality of internal passageways, a plurality of nozzles extending from the lower surface, and a nozzle extending from the upper surface. Each of the nozzles extending from the lower surface is in communication with one of the internal passageways. The nozzle extending from the upper surface is also in communication with the internal passageways.

The frame is movable from a first location overlying an egg flat to a second location overlying an area adjacent the egg flat. When the frame is in the first location, eggs from an egg flat are picked up under vacuum via a plurality of flexible cups secured to each nozzle extending from the lower surface. Vacuum is provided within the internal passageways via the nozzle extending from the upper surface. When the frame is in the second position, the eggs are released from the plurality of flexible cups by introducing positive air pressure within the internal passageways via the nozzle extending from the upper surface.

According to another embodiment of the present invention, an egg may be lifted from an egg flat via a flexible cup under vacuum and then propelled into a receptacle or discharge ramp via a horizontal stream of air.

Removable manifolds according to the present invention can be quickly and easily removed from a supporting frame and cleaned as a unit. Accordingly, time consuming and labor intensive cleaning efforts typically required by conventional egg removal devices can be eliminated.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 14 is a top plan view of an egg removal apparatus according to another embodiment of the present invention.

FIG. 15 is a side elevation view of the egg removal apparatus of FIG. 14.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
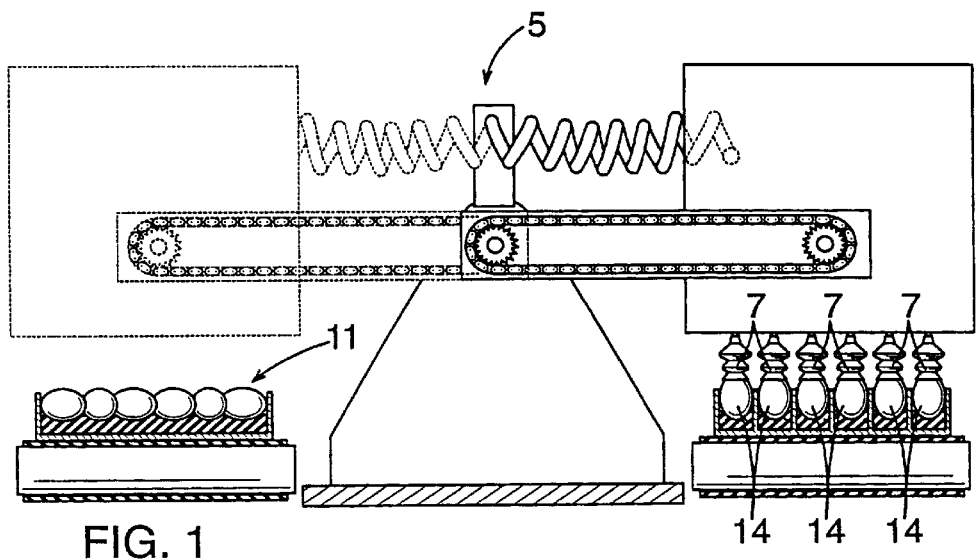
FIG. 1 is a side elevational view of a conventional apparatus for removing eggs from an egg flat.
Figure 2A:
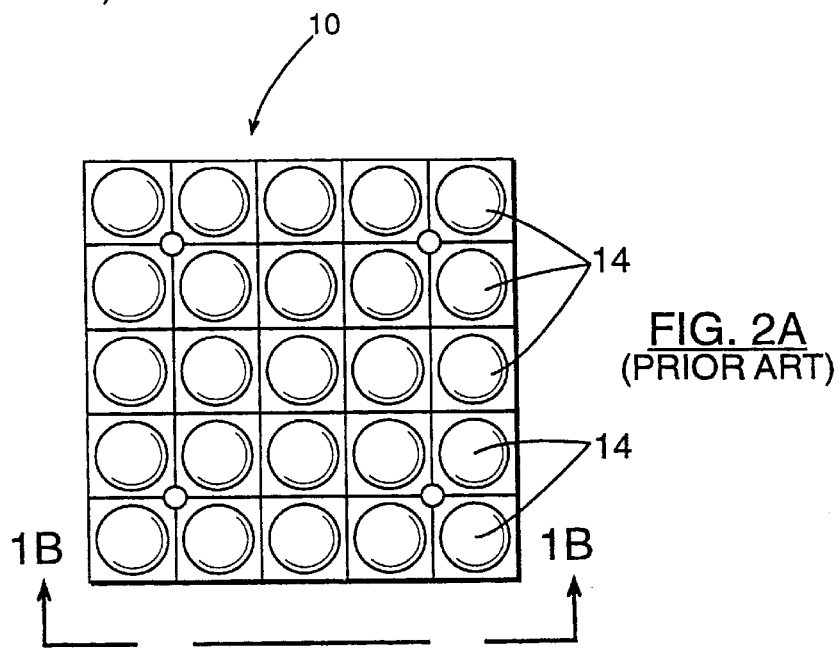
FIG. 2A is a top plan view of an egg flat configured to carry twenty-five eggs in an array of five rows of five eggs each, wherein each egg is supported in a substantially vertical position.
Figure 2B:
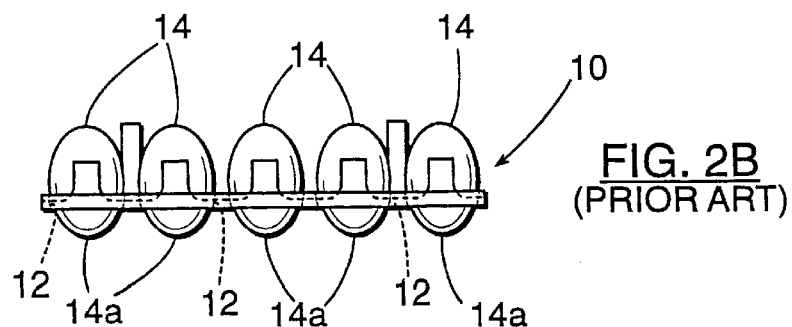
FIG. 2B is a side elevation view of the flat of FIG. 2A.

The present invention may be utilized with any type of avian eggs, including, but not limited to, chicken, turkey, duck, geese, quail, and pheasant eggs. The present invention is particularly adapted for use with egg carriers often referred to as "flats." An exemplary egg flat 10 is illustrated in FIGS. 2A and 2B. The illustrated egg flat 10 includes a plurality of rows of apertures 12. Each aperture 12 is configured to receive one end 14a of a respective egg 14 so as to support the respective egg 14 in a substantially vertical position (FIG. 2B), typically with the internal egg air cell disposed upwardly.

The illustrated egg flat 10 carries twenty-five eggs in an array of five rows of five eggs each. However, an egg flat used in accordance with the present invention may contain any number of rows containing any number of eggs. Furthermore, eggs in adjacent rows may be parallel to one another, as in a "rectangular" flat, or may be in a staggered relationship, as in an "offset" flat. Examples of commercial egg flats with which the present invention may be used include, but are not limited to, the "CHICKMASTER 54" flat, the "JAMESWAY 42" flat, and the "JAMESWAY 84" flat (in each case, the number indicates the number of eggs carried by the egg flat).

It is to be understood that, for each of the below described embodiments of the present invention, eggs can be removed from an egg flat while the egg flat is moving, either continuously or otherwise, or is stationary. Furthermore, the present invention is not limited to the illustrated directions of egg flat travel in the below described embodiments of the present invention. Egg flats may travel in various directions relative to an apparatus for removing eggs therefrom.

Figure 3:
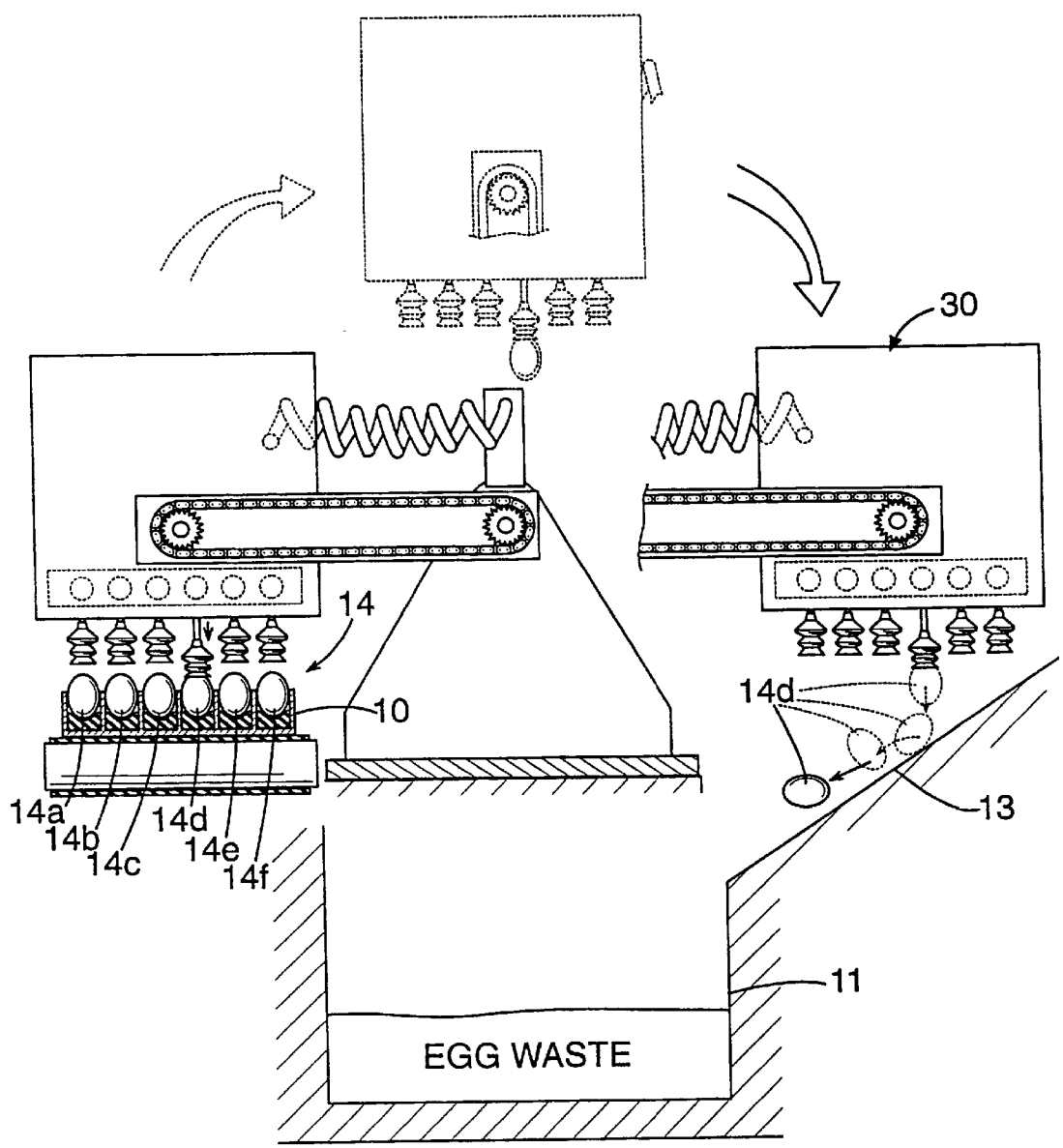
FIG. 3 is a side elevational view of an apparatus for removing eggs from an egg flat, according to an embodiment of the present invention, and illustrating movement of the apparatus from a first location overlying an egg flat to a second location overlying a receptacle for receiving eggs removed from the egg flat.

Referring now to FIG. 3, an egg removal apparatus 30 that is configured to engage and lift individual eggs from an egg flat, according to an embodiment of the present invention, is illustrated. In the illustrated embodiment, the egg removal apparatus 30 is movable between a first location overlying an egg flat and a second location overlying a ramp 13 that leads to a waste receptacle 11. In this embodiment, clear eggs, or eggs having other defects, can be removed from an egg flat and disposed of. However, as would be understood by those skilled in the art, the egg removal apparatus 30 of the present invention may also be utilized for transferring eggs from an egg flat to various other receptacles, such as hatching trays, and the like.

Figure 4:
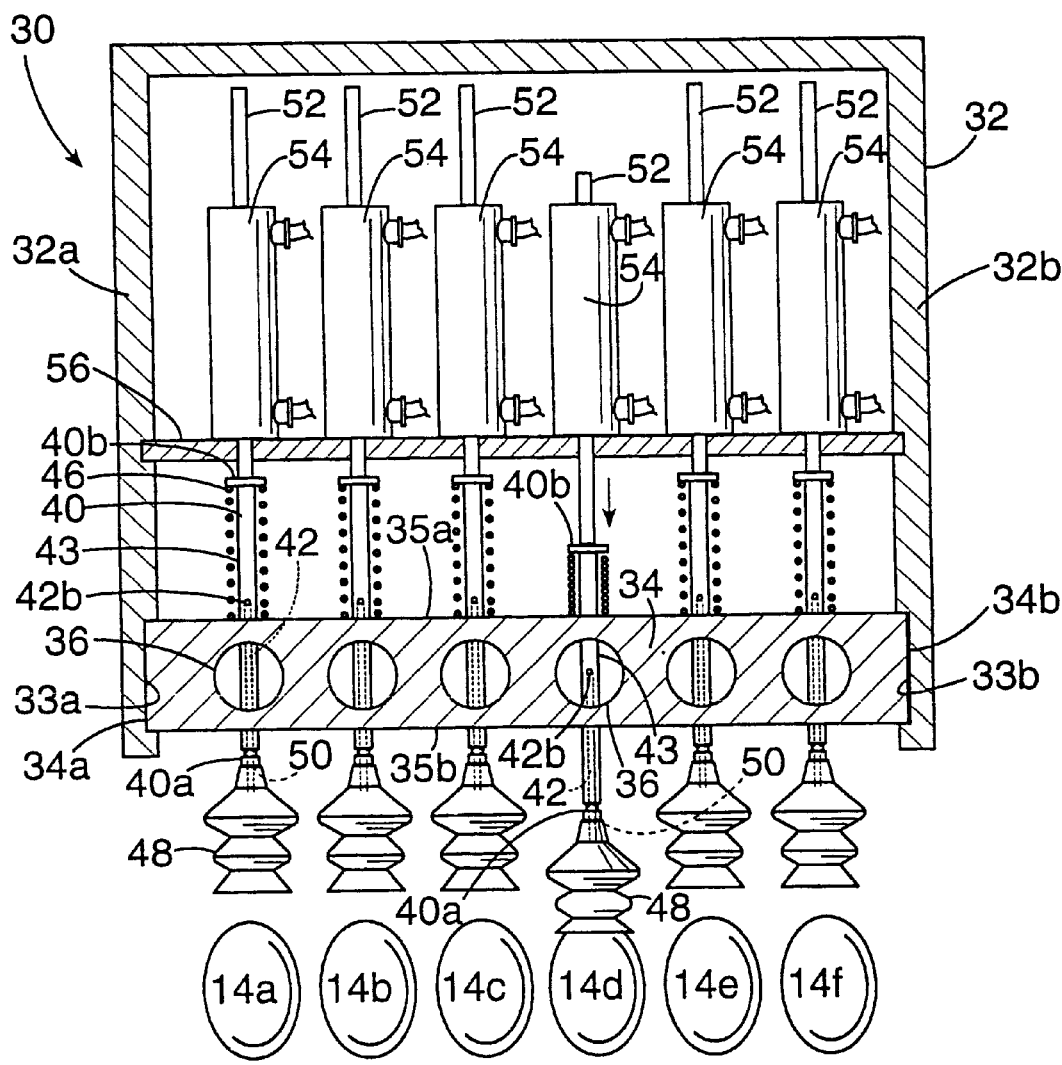
FIG. 4 is a cross-sectional view of an apparatus according to an embodiment of the present invention illustrating a removable manifold.
Figure 5:
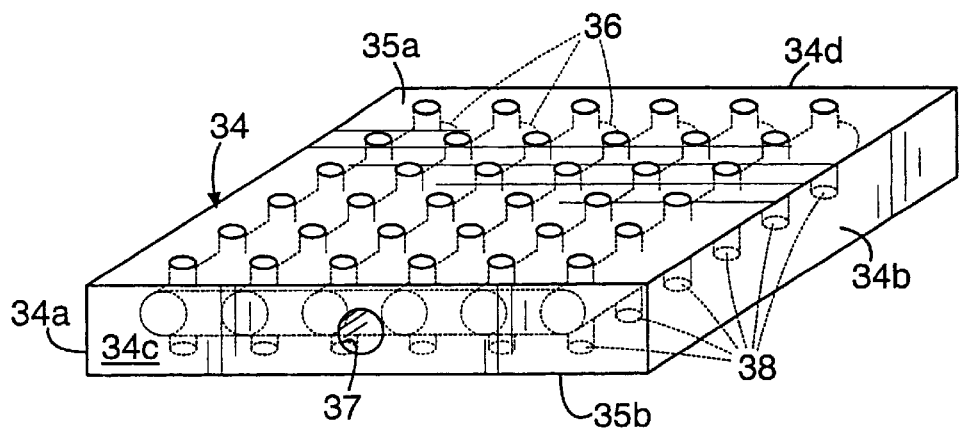
FIG. 5 is a perspective view of a set of internal passageways and a plurality of plunger bores in the manifold of FIG. 4.

Referring now to FIGS. 4 and 5, the egg removal apparatus 30 of FIG. 3 is illustrated in greater detail. The egg removal apparatus 30 includes a frame 32 and a manifold 34 removably secured to the frame 32. The manifold 34 includes opposite side walls 34a, 34b, opposite end walls 34c, 34d (FIG. 5), and opposite upper and lower surfaces 35a, 35b. The frame 32 includes opposite side walls 32a, 32b having opposite grooves 33a, 33b formed therein as illustrated. The removable manifold 34 is configured to slide between, and be retained by, the grooves 33a, 33b as illustrated. The frame and the manifold may be formed from various materials, including, but not limited to, metals and polymers.

The manifold 34 includes a plurality of internal passageways 36 that terminate at an aperture 37 in an end wall 34c of the manifold 34 (FIG. 5). The internal passageways 36 are intended to be alternately maintained under vacuum and positive air pressure, as will be described below. Vacuum within the internal passageways 36 may be provided by a vacuum pump or other vacuum source in communication with the aperture 37.

Figure 6:
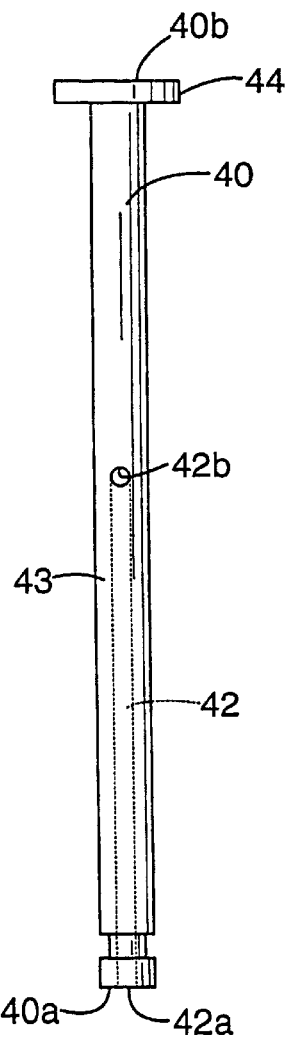
FIG. 6 is an enlarged, side elevational view of a plunger supported for reciprocal movement in a plunger bore in the manifold of FIG. 4.

A plurality of plunger bores 38 (FIG. 5) extend from the manifold upper surface 35a to the lower surface 35b such that each plunger bore 38 is in communication with one of the internal passageways 36 as illustrated in FIG. 4. Each plunger bore 38 is configured to receive a respective elongated plunger 40 therewithin. Each plunger 40 includes opposite first and second ends 40a, 40b and an axially-extending internal bore 42. The internal bore 42 terminates at a first port 42a in the plunger first end 40a and at an opposite second port 42b in a medial portion 43 of the plunger 40 between the first and second ends 40a, 40b as illustrated in FIG. 6.

As illustrated in FIG. 4, each plunger 40 is supported for reciprocal movement between a first and second position in a respective plunger bore 38. Clearance between a plunger 40 and a respective plunger bore 38 is preferably between about 0.001 inches and about 0.006 inches to allow free motion of a plunger 40 within a plunger bore 38 without causing excessive air loss therebetween. However, other clearances may be acceptable. In the illustrated embodiment, each plunger second end 40b includes a shoulder 44 (FIG. 6). A spring 46 positioned coaxially around each plunger 40 is retained at one end by the shoulder 44 and at the opposite end by the upper surface 35a of the manifold 34. As will be described below, each spring 46 serves as means for automatically returning a respective plunger 40 from the second position to the first position upon removal of a downwardly directed force applied to the plunger second end 40b.

A flexible cup 48 is secured to the first end 40a of each plunger 40, via an aperture 50 in each flexible cup 48, as illustrated in FIG. 4. Each flexible cup 48, thus, is in communication with an internal bore 42 of a plunger 40 to which the flexible cup 48 is secured. Accordingly, as will be described below, vacuum can be provided to each flexible cup 48 via an internal bore 42 of a plunger 40 to which the flexible cup 48 is secured. Exemplary flexible cups 48 are available from Diamond Automation, Farmington Hill, Mich.

As illustrated in FIG. 4, a pneumatically-operated piston 52, which serves as means for moving each plunger from the first position to the second position, is positioned above each plunger 40. Each piston 52, when activated via a respective pneumatic cylinder 54, is configured to apply a downwardly directed force to a respective plunger second end 40b so as to move the plunger 40 downward within a respective plunger bore 38. In the illustrated embodiment, each pneumatic cylinder 54 is secured to a plate 56 extending between the side walls 32a, 32b of the frame 32. However, it is understood that the present invention is not limited to the illustrated embodiment. Furthermore, it is understood that each piston 52 may be actuated in various ways, including but not limited to, mechanical actuators, hydraulic actuators, and electrical actuators. Exemplary pneumatically-operated pistons 52 are available from Clippard Instrument Laboratory, Cincinnati, Ohio.

As illustrated in FIG. 4, when a plunger 40 is in the first position, the second port 42b in a medial portion 43 of the plunger 40 is not in communication with a respective internal passageway 36. When a plunger 40 is moved from the first position to the second position via a respective piston 52, the second port 42b, and thus the plunger internal bore 42, is in communication with a respective internal passageway 36. When vacuum is provided within the internal passageway 36, vacuum is supplied to a flexible cup 48 via the internal bore 42. Accordingly, when a plunger 40 is moved from the first position to the second position the flexible cup 48 secured to the plunger first end 40a is configured to engage an egg 14 and via suction retain an egg 14 in seated relation therewith. The amount of vacuum supplied to each cup 48 is preferably sufficient to lift an egg 14 and transfer the egg 14 to another location.

To release an egg 14, positive air pressure can be applied to the internal passageways 36 while a plunger 40 is maintained in the second position. An external valve (not illustrated) may be utilized to provide the internal passageways 36 with positive air pressure. Alternatively, a plungers 40 can be returned to the first position whereupon vacuum is destroyed because the plunger internal bore 42, and thus the flexible cup 48, is exposed to atmospheric pressure.

In FIG. 4, the plungers 40 positioned directly above eggs 14a, 14b, 14c, 14e and 14f are maintained in the first position via respective springs 46. The plunger 40 directly above egg 14d has been moved to the second position via the piston 52, as illustrated. In the second position, the plunger second aperture 42b is in communication with an internal passageway 36, which is maintained under vacuum, and the flexible cup 48 has moved downwardly to engage egg 14d.

Referring back to FIG. 3, the egg removal apparatus 30 is illustrated with the egg 14d being lifted from the egg flat 10 (i.e., the first location) via the middle flexible cup 48 and plunger 40 which have been moved to the second position. The egg removal apparatus 30 is translated to a second location overlying a ramp 13 that leads to a receptacle 11, whereupon the egg 14d is released from the flexible cup 48. As described above, the egg 14d may be released by either introducing positive air pressure into the internal passageways 36 while the plunger 40 is maintained in the second position, or by returning the plunger 40 to the first position.

The present invention is advantageous because the manifold 34, along with plungers 40 and flexible cups 48, can be easily removed from the supporting frame 32 and placed within a bath as a unit for cleaning. Furthermore, the internal passageways and plunger bores are configured to permit cleaning fluid to move effectively therethrough.

The present invention may be utilized for removing selected eggs from an egg flat. For example, clear eggs, identified via a clear egg identification system, may be selectively removed from an egg flat via an egg removal apparatus according to the present invention. An exemplary clear egg identification system is described in co-assigned U.S. Pat. No. 5,745,228 to Hebrank et al., the disclosure of which is incorporated herein by reference in its entirety.

Figure 7:
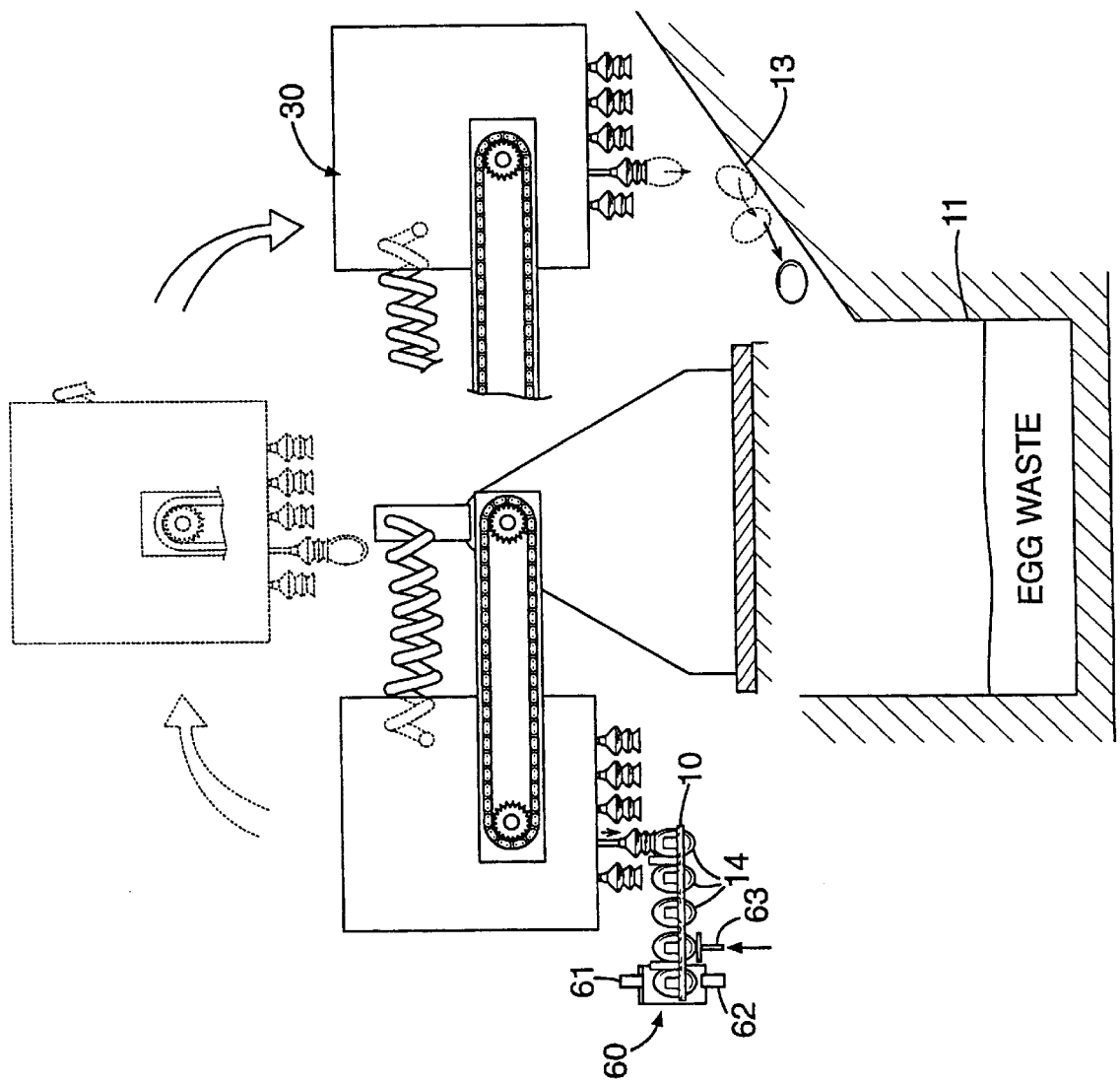
FIG. 7 is a side elevational view of an apparatus incorporating the manifold of FIGS. 4–5 wherein the frame is shown moving between a first location, wherein eggs are removed from an egg flat, and a second location, wherein the eggs are deposited within a receptacle.

FIG. 7 illustrates a clear egg identification system 60 used in conjunction with an egg removal device 30, according to the present invention. The illustrated clear egg identification system 60 includes a plurality of light sources 61 positioned on one side of the egg flat 10 and a corresponding plurality of light detectors 62 positioned on the other side of the egg flat 10 opposite the light sources 61. The light detectors 62 are configured to identify clear eggs based upon an amount of light from a respective light source 61 that passes through an egg 14.

It is understood that the positions of the illustrated light sources 61 and light detectors 62 are not critical and may be reversed. In addition, a light source 61 and light detector 62 may be placed in different orientations, so long as light from a light source 61 can pass through an egg 14 to a light detector 62.

In addition, other devices for detecting clear eggs, as well as eggs with other characteristics, can be utilized with the present invention. For example, U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 4,671,652 to van Asselt et al. describes a candling apparatus in which a plurality of light sources and corresponding light detectors are mounted in an array, and the eggs passed on a flat between the light sources and the light detectors.

Eggs that are in a "stuck" condition within an egg flat may require more force to remove than can be provided via the "pull" of a flexible cup under vacuum. According to another aspect of the present invention, a member 63, such as a pneumatic bellows or piston, may utilized as means for dislodging an egg 14, as illustrated in FIG. 7. The illustrated member 63 is configured to apply an upwardly directed force on an egg to release the egg 14 from a stuck condition. This upwardly directed force may be applied separately or in combination with the pull of a flexible cup 48 under vacuum. Various devices for applying an upwardly directed force to an egg to release the egg from a stuck condition may be utilized.

Figure 8:
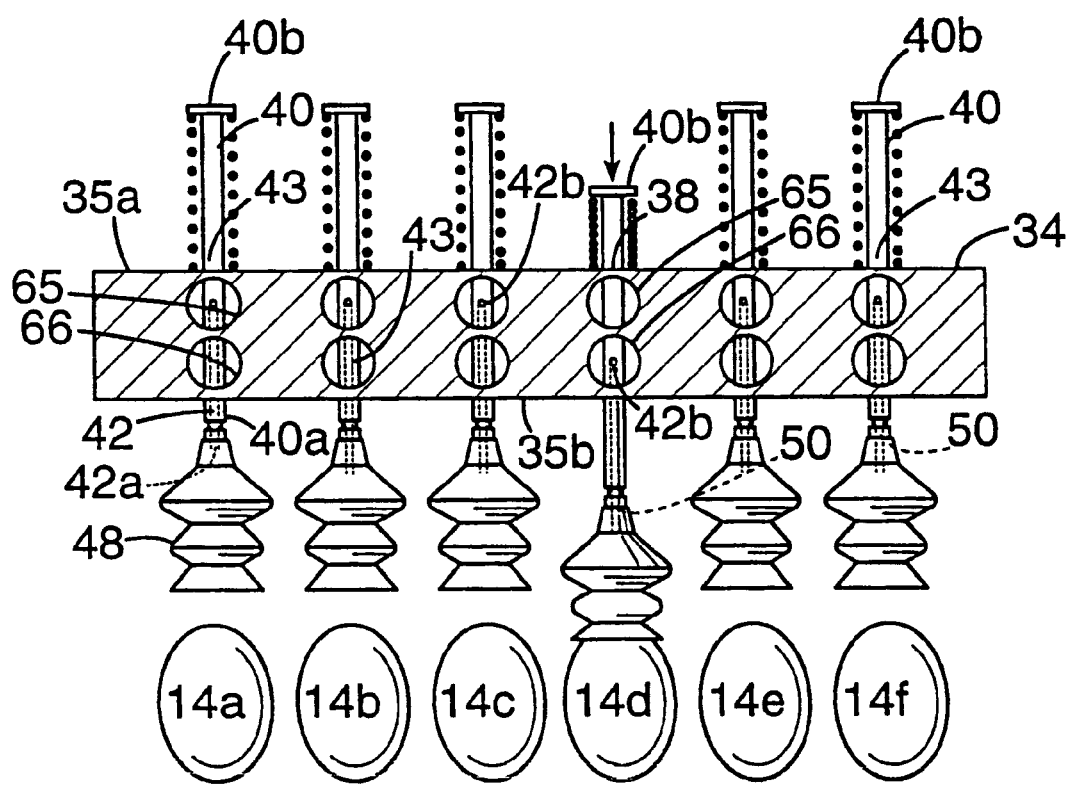
FIG. 8 is a cross-sectional view of a removable manifold according to another embodiment of the present invention wherein the manifold includes first and second sets of internal passageways.
Figure 9:
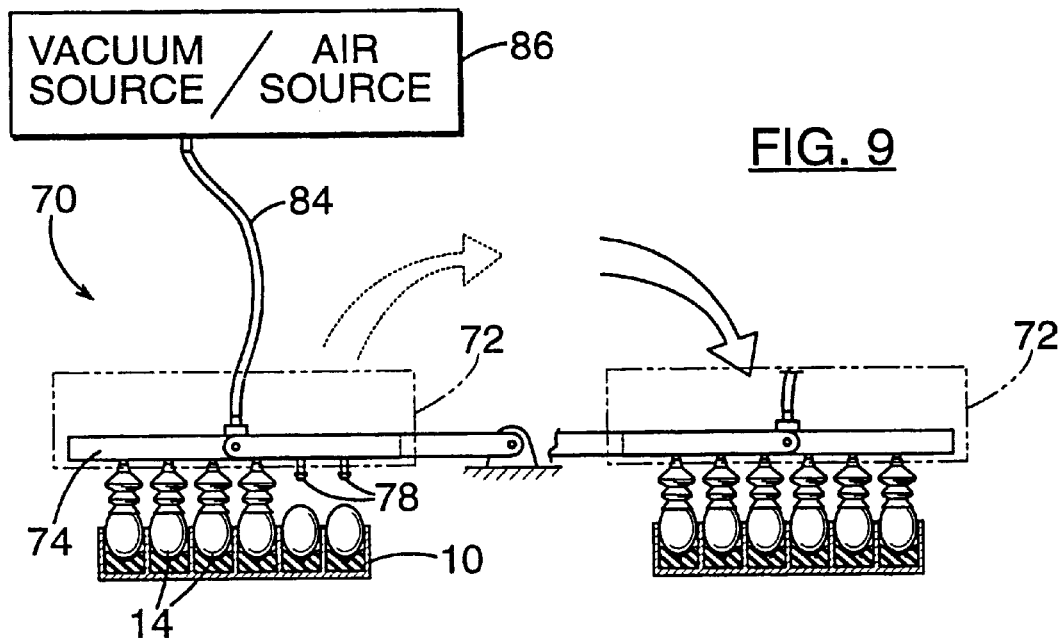
FIG. 9 is a side elevational view of an egg removal apparatus incorporating a removable manifold according to another embodiment of the present invention.
Figure 10:
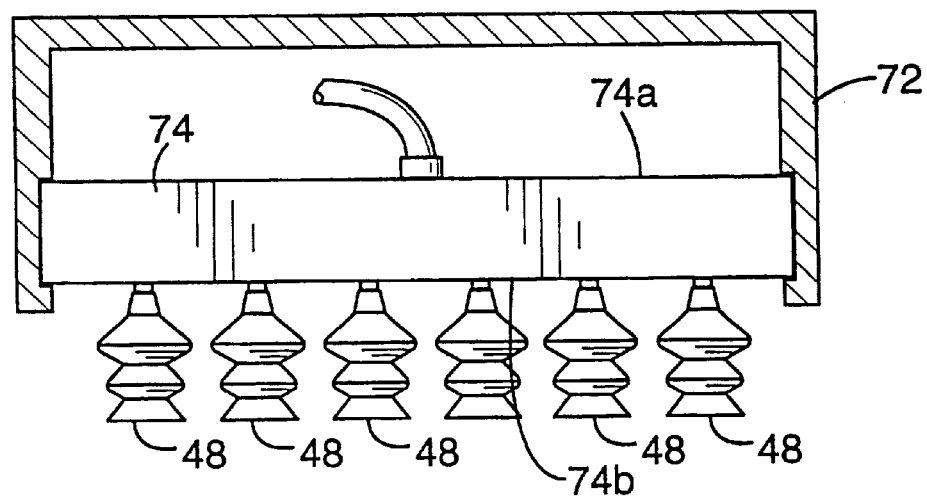
FIG. 10 is a front elevational view of the egg removal apparatus of FIG. 9 taken along lines 10—10.

Referring now to FIG. 8, a removable manifold 34 according to another embodiment of the present invention is illustrated. The illustrated manifold 34 includes opposite upper and lower surfaces 35a, 35b and first and second sets of internal passageways 65, 66. A plurality of plunger bores 38 extend from the upper surface 35a to the lower surface 35b. Each plunger bore 38 is in communication with one of the first and second internal passageways 65, 66. Positive air pressure is maintained within the first set of internal passageways 65. Vacuum is maintained within the second set of internal passageways 66.

Each plunger bore 38 is configured to receive a respective elongated plunger 40 therewithin. Each plunger 40 includes opposite first and second ends 40a, 40b and an axially-extending internal bore 42. The internal bore 42 terminates at a first port 42a in the plunger first end 40a and at an opposite second port 42b in a medial portion 43 of the plunger 40 between the first and second ends 40a, 40b, as described above.

Each plunger 40 is supported for reciprocal movement between a first and second position in a respective plunger bore 38 via a spring 46, as described above. In the first position, the second port 42b of each plunger 40 is in communication with a respective one of the first set of internal passageways 65. In the second position, the second port 42b of each plunger 40 is in communication with a respective one of the second set of internal passageways 65.

A flexible cup 48 is secured to the first end 40a of each plunger 40, via aperture 50, as illustrated. Each flexible cup 48 is in communication with an internal bore 42 of a plunger 40 to which the flexible cup 48 is secured. Accordingly, positive air pressure can be provided to each flexible cup 48 via internal bore 42 when the plunger 40 is in the first position. Similarly, vacuum can be provided to each flexible cup 48 via internal bore 42 when the plunger 40 is in the second position.

In FIG. 8, the plungers 40 positioned directly above eggs 14a, 14b, 14c, 14e and 14f are maintained in the first position via respective springs 46. The plunger 40 directly above egg 14d has been moved to the second position such that the second aperture 42b is in communication with one of the second set of internal passageways 66 and the flexible cup 48 is in contact with the egg 14d. The flexible cup 48 retains the egg 14d in seated relation therewith because of the vacuum provided to the flexible cup 48 via the internal bore 42. The amount of vacuum supplied to the flexible cup 48 is sufficient to lift the egg 14d and transfer the egg 14d to another location. To release the egg 14d from the flexible cup 48, the plunger 40 is moved to the first position so that positive air pressure is introduced into the flexible cup 48 via the internal bore 42, which is now in communication with one of the first set of internal passageways 65. Accordingly, vacuum within the flexible cup is destroyed and the egg 14d is released.

Referring now to FIGS. 9–13, another embodiment of the present invention is illustrated. In this embodiment, an apparatus 70 for removing eggs 14 from an egg flat 10 includes a frame 72 and a manifold 74 removably secured to the frame 72. The frame 72 is movable from a first location overlying an egg flat 10 to a second location overlying an area adjacent the egg flat, as illustrated. When the frame 72 is in the first location, eggs 14 from an egg flat 10 are picked up under vacuum via a plurality of flexible cups 48. When the frame 72 is in the second location, the eggs 14 are released from the plurality of flexible cups 48.

Figure 11:
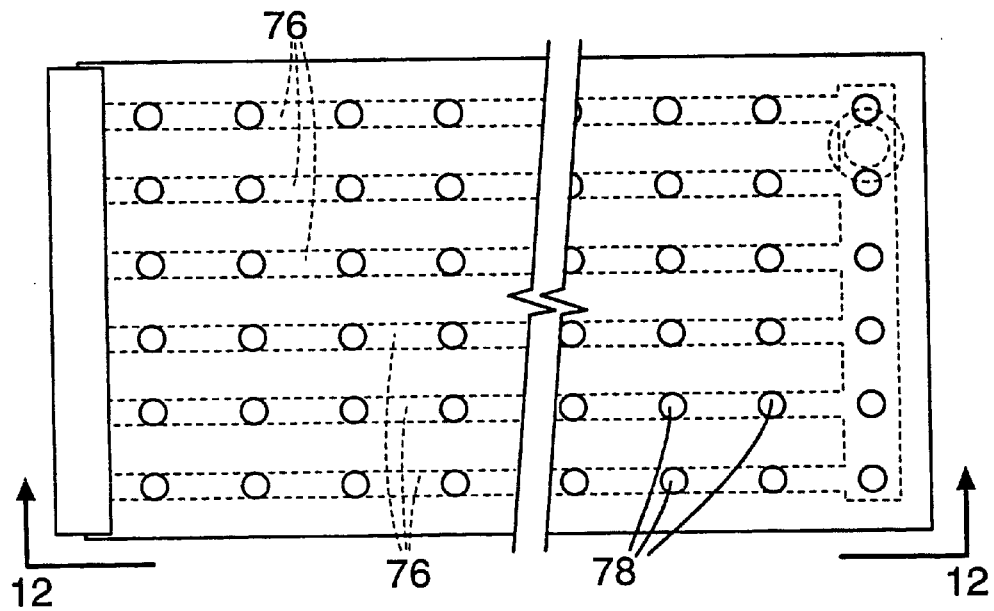
FIG. 11 is a bottom plan view of the removable manifold of FIG. 9 illustrating the plurality of internal passageways and the plurality of ports in the lower surface of the manifold that are in communication with the plurality of internal passageways.
Figure 12:
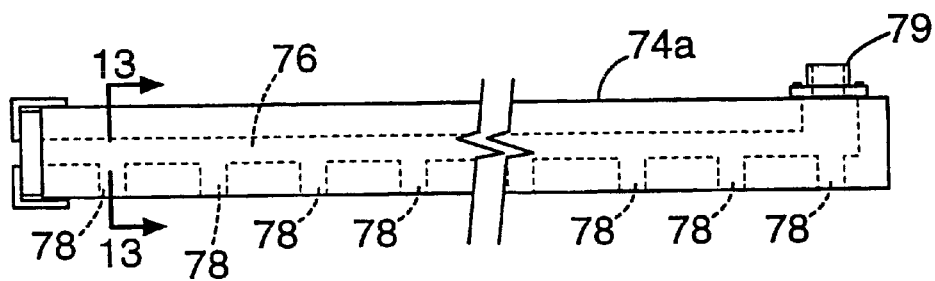
FIG. 12 is a side elevational view of the removable manifold of FIG. 11 taken along lines 12—12.
Figure 13:
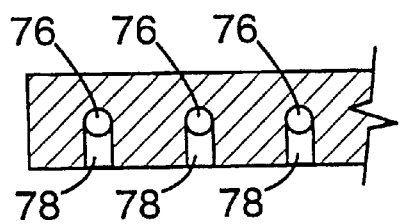
FIG. 13 is a sectional view of the removable manifold of FIG. 12 taken along lines 13—13.

The removable manifold 74 includes opposite upper and lower surfaces 74a, 74b and a plurality of internal passageways 76, as illustrated in FIGS. 11–13. Each one of the internal passageways 76 includes a plurality of ports 78 that extend to the manifold second surface 74b. Each of these ports 78 is configured to receive a respective first nozzle 80 (FIG. 10) therein. A second nozzle 79 (FIG. 12) extends from the upper surface 74a and is in fluid communication with the plurality of internal passageways 76.

A flexible cup 48 is secured to each respective first nozzle 80 such that each flexible cup 48 is in communication with a respective one of the internal passageways 76. Each flexible cup 48 is configured to engage and retain an egg in seated relation therewith when the frame 72 is in the first position and when vacuum is supplied within the internal passageways via a conduit 84 that establishes fluid communication between a vacuum source 86 and the manifold second nozzle 79. When the frame 72 is moved to the second location, eggs 14 can be released from the plurality of flexible cups 48 by destroying the vacuum within each flexible cup 48. Vacuum can be destroyed by introducing positive air pressure within the internal passageways 76 via the conduit 84 that is in fluid communication with an air source 86.

Referring now to FIGS. 14–15, another embodiment of the present invention is illustrated. In this embodiment, an apparatus 130 for removing eggs 14 from an egg flat 10 that is moving in a substantially horizontal direction (indicated by arrow 131) includes a frame 32 and a manifold 34 removably secured to the frame 32. A receptacle 133 is positioned above the egg flat 10 and adjacent the frame 32, as illustrated. The receptacle 133 may be a ramp that leads to an egg disposal area. Alternatively, the receptacle 133 may include a conveyor belt for transporting eggs removed from an egg flat to another location.

The illustrated manifold 34 is similar to that described with respect to FIG. 8. The illustrated manifold 34 includes opposite upper and lower surfaces 35a, 35b and first and second sets of internal passageways 65, 66. A plurality of plunger bores 38 extend from the upper surface 35a to the lower surface 35b. Each plunger bore 38 is in communication with one of the first and second internal passageways 65, 66. Positive air pressure is maintained within the first set of internal passageways 65. Vacuum is maintained within the second set of internal passageways 66.

Each plunger bore 38 is configured to receive a respective elongated plunger 40 therewithin. Each plunger 40 includes opposite first and second ends 40a, 40b and an axially-extending internal bore 42 (illustrated in detail in FIG. 6). The internal bore 42 terminates at a first port 42a in the plunger first end 40a and at an opposite second port 42b in a medial portion 43 of the plunger 40 between the first and second ends 40a, 40b, as described above.

Each plunger 40 is supported for reciprocal movement between a first and second position in a respective plunger bore 38. In the first position, the second port 42b of each plunger 40 is in communication with a respective one of the first set of internal passageways 65. In the second position, the second port 42b of each plunger 40 is in communication with a respective one of the second set of internal passageways 65.

A flexible cup 48 is secured to the first end 40a of each plunger 40, via aperture 50, as illustrated. Each flexible cup 48 is in communication with an internal bore 42 of a plunger 40 to which the flexible cup 48 is secured. Accordingly, positive air pressure can be provided to each flexible cup 48 via internal bore 42 (FIG. 6) when the plunger 40 is in the first position. Similarly, vacuum can be provided to each flexible cup 48 via internal bore 42 when the plunger 40 is in the second position.

The illustrated egg removal apparatus 130 includes a source or supply of pressurized air 140, which is configured to maintain a substantially constant air pressure. A set of air lines 142 extend from the pressurized air supply 140. Each of the air lines preferably includes a nozzle 144 that is positioned adjacent a respective egg 14 retained in seated relation with a respective flexible cup 48. Preferably, each nozzle 144 is positioned between about one-quarter inch (0.25") and about three inches (3.0") from a respective egg 14 and indicated as D in FIG. 14.

According to a preferred embodiment of the present invention, each air line 142 in the set is formed from tubing (e.g., stainless steel tubing, or copper tubing) having an inner diameter of between about 0.1875 inches and about 0.5 inches. Each nozzle 144 is preferably a one-eighth inch (⅛") NPT (National Pipe Thread) fitting (Eldon James, Loveland, Colo.). In the illustrated embodiment, each nozzle 144 has an end portion 144a with a generally straight configuration. However, it is to be understood that the nozzles 144 may each have end portions 144a with various configurations, such as a diverging configuration.

The air supply 140 preferably is a tank having a volume of between about five (5) gallons and about twenty (20) gallons to ensure that pressure is maintained substantially constant during the period of time that air is applied to an egg to eject the egg into the receptacle.

As illustrated in FIG. 14, each nozzle 144 may be oriented along a direction that is substantially transverse to the horizontal direction 131 of the moving egg flat 10. Each air line 142 also preferably includes a valve 146 located between a respective nozzle 144 and the air supply 140. Each valve 146 serves as means for controlling a stream of air from the pressurized air supply 140 through a nozzle 144 for a predetermined period of time. A particularly preferred valve for controlling a stream of air from the pressurized air supply 140 through a nozzle 144 is a 0.5 inch poppet valve manufactured by Spartan Scientific, Youngstown, Ohio. However, it is understood that the present invention is not limited to the use of poppet valves. Various types of valves may be utilized in carrying out the present invention.

Figure 16:
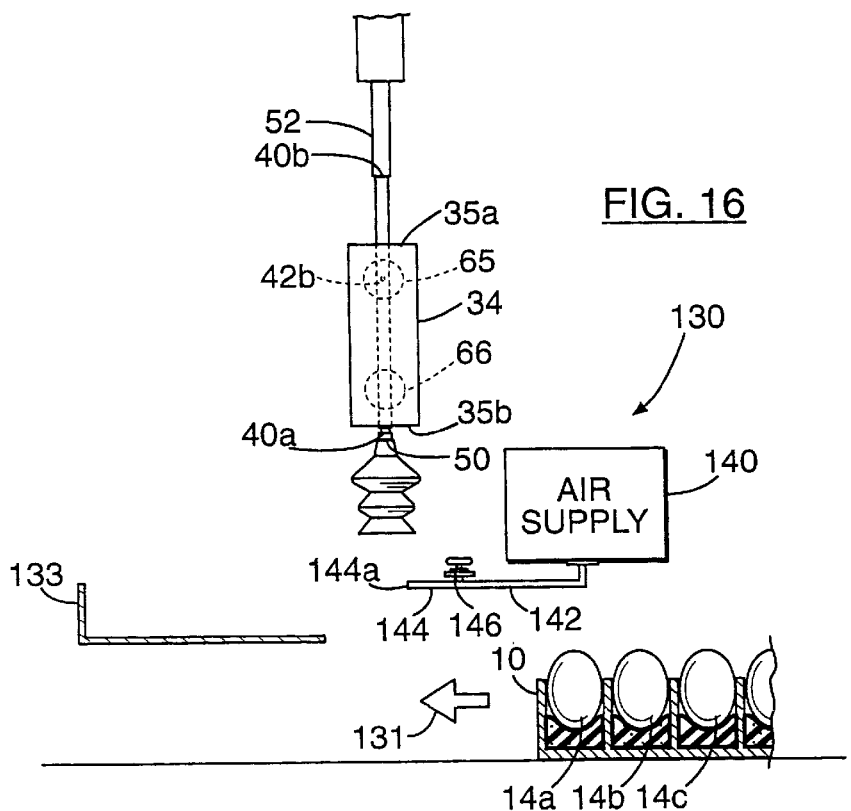
FIGS. 16–19 illustrate operations for removing an egg from an egg flat via the egg removal apparatus of FIG. 14.
Figure 17:
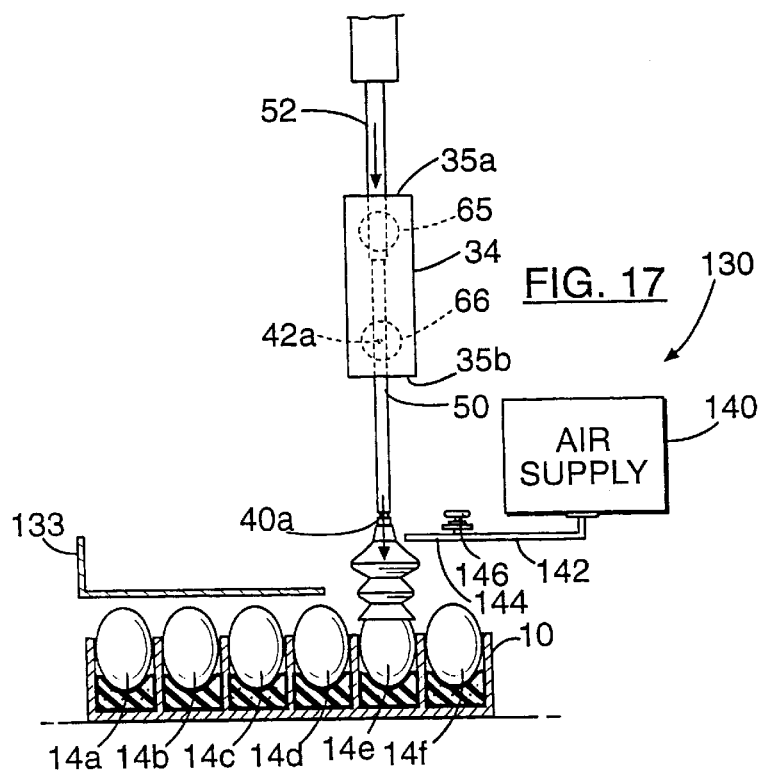

Referring to FIGS. 16–19, removal of an egg from a moving egg flat via the apparatus of FIGS. 14–15 will now be described. In FIG. 16, an egg flat 10 containing a plurality of eggs 14 is moving along a horizontal direction 131. In FIG. 17, the egg flat 10 (either stationary or moving) is located such that a flexible cup 48 is positioned above egg 14e. As illustrated, the plunger 40 is moved downwardly via actuator 52 so that the flexible cup 48 contacts the egg 14e. The second port 42b in the plunger 40 is in communication with the second internal passageway 66. As described above, the second internal passageway 66 is under vacuum. Accordingly, as described above, vacuum is provided into the flexible cup 48 via the plunger internal bore 42 to maintain the egg 14e in seated relation therewith.

Figure 18:
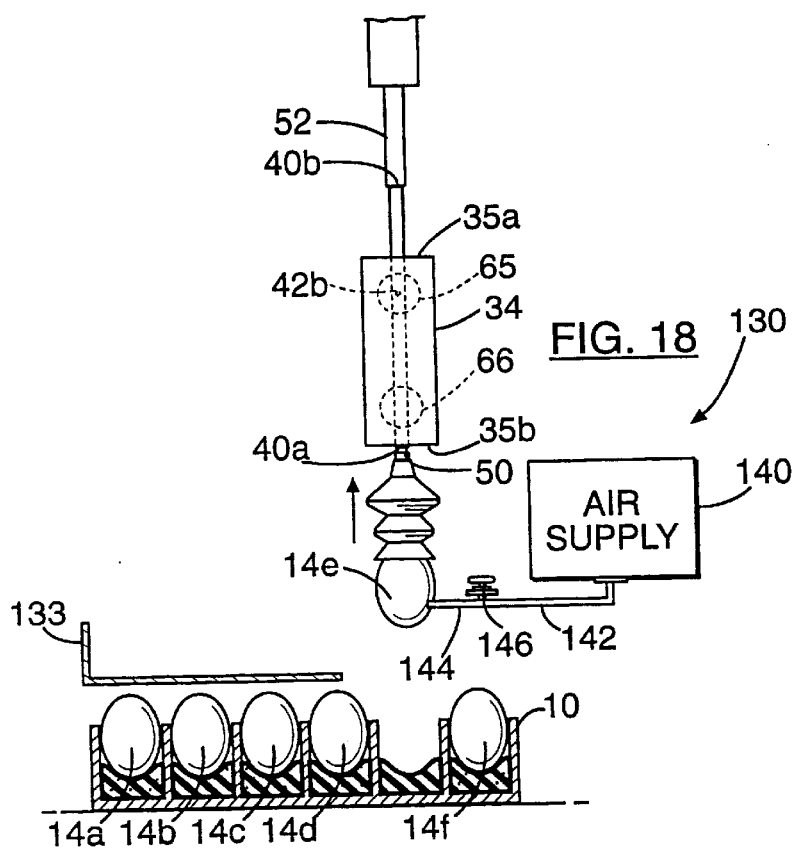
Figure 19:
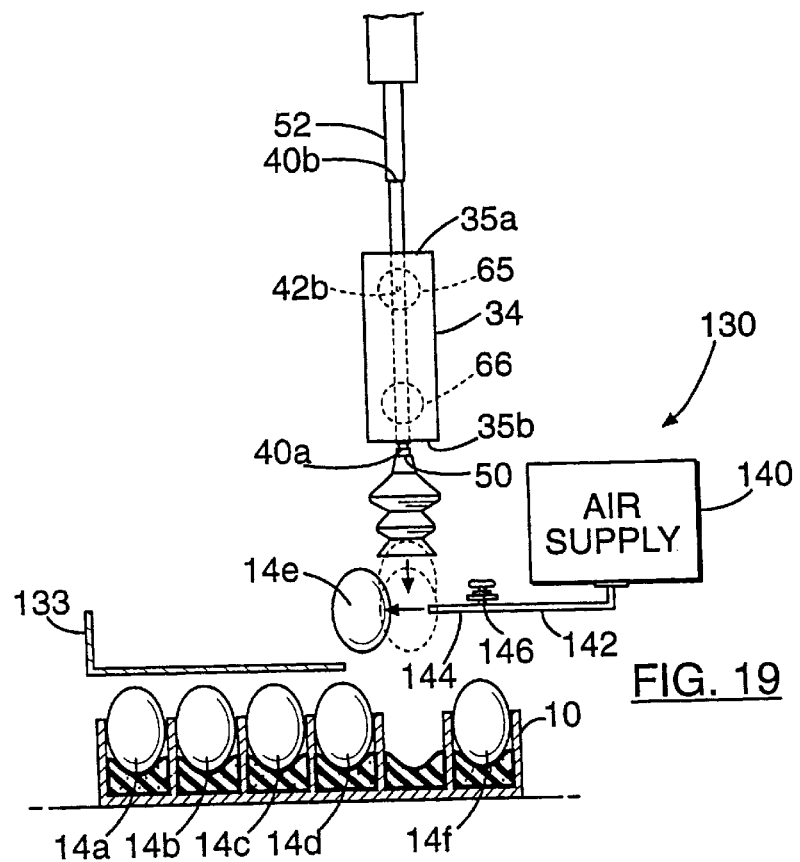

In FIG. 18, the plunger 40 is moved upwardly towards the first position. When the second port 42b in the plunger establishes communication with the manifold first internal passageway 65, vacuum within the flexible cup 48 is destroyed (as described above) and the egg 14e is released from the flexible cup. At about the same time that the second port 42b establishes communication with the manifold first internal passageway 65, a horizontal stream of air is applied to the egg 14e to propel the egg 14e into the receptacle 133, as illustrated in FIG. 19. Preferably, a stream of air has a duration of between about 50 milliseconds and about 300 milliseconds.

Figure 20:
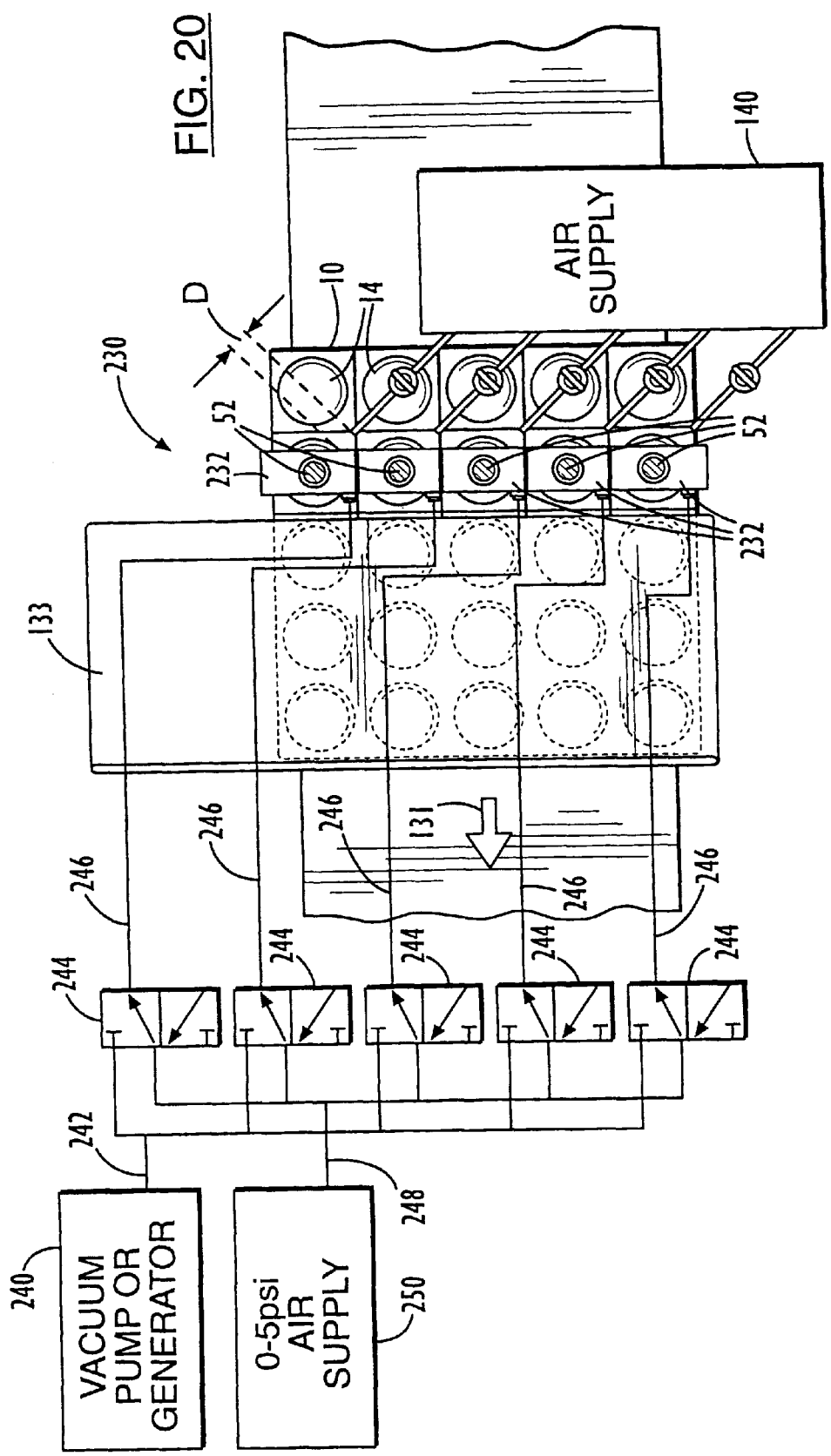
FIG. 20 is a top plan view of an egg removal apparatus according to another embodiment of the present invention.
Figure 21:
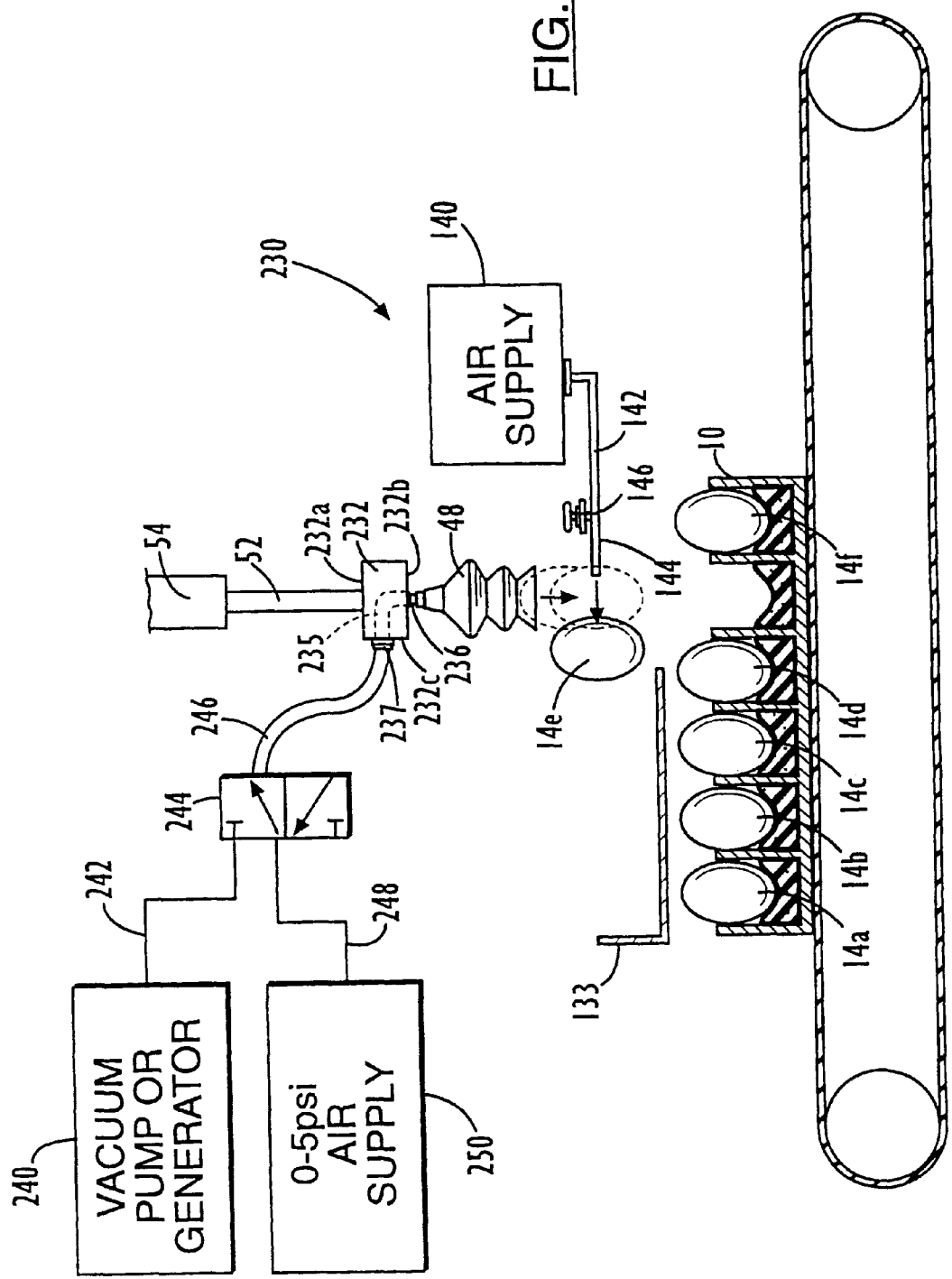
FIG. 21 is a side elevation view of the egg removal apparatus of FIG. 20.

Referring now to FIGS. 20–21, another embodiment of the present invention is illustrated. In this embodiment, an apparatus 230 for removing eggs 14 from an egg flat 10 that is moving (preferably continuously) in a substantially horizontal direction (indicated by arrow 131) includes a plurality of manifold blocks 232, each positioned above a respective egg 14 in the egg flat 10 and each supported for reciprocal movement between first and second positions.

A receptacle 133 is positioned above the egg flat 10 and adjacent the manifold blocks 232, as illustrated. The receptacle 133 may be a ramp that leads to an egg disposal area. Alternatively, the receptacle 133 may include a conveyor belt for transporting eggs removed from an egg flat to another location.

Each illustrated manifold block 232 includes opposite upper and lower surfaces 232a, 232b and an internal passageway 235 that terminates at a first nozzle 236 extending from the lower surface 232b and an opposite second nozzle 237 extending from a side surface 232c thereof.

A flexible cup 48 is secured to a first nozzle 236 extending from each manifold block 232, as illustrated. Each flexible cup 48 is in communication with the internal passageway 235 within a respective manifold block 232. Accordingly, positive air pressure can be provided to each flexible cup 48 via the internal passageway 235 and vacuum can be provided to each flexible cup 48 via the internal passageway 235.

In the illustrated embodiment, a source or supply of vacuum 240 provides vacuum to each manifold block 232 via the second nozzle 237. Similarly, a source or supply of pressurized air 250 provides pressurized air to each manifold block 232 via the second nozzle 237. In the illustrated configuration, a vacuum line 242 extends between the vacuum source 240 and each valve 244. However, individual vacuum generators may also be used to supply vacuum to each valve 244. An air/vacuum line 246 extends between each valve 244 and the second nozzle 232 of each manifold block 232. Similarly, an air line 248 extends between the pressurized air source 250 and each valve 244. An exemplary valve 244 includes model VQ21A1-5G-C8 solenoid driven valves by SMC Pneumatics, Inc., 3011 North Franklin Road, Indianapolis, Ind.

In operation, each valve 244 is configured to provide vacuum to the internal passageway 235 of each manifold block 232 when each manifold block is in the second position such that a respective egg 14 can be retained in seated relation therewith as described above. Each valve 244 is also configured to provide pressurized air to the internal passageway 235 of each manifold block 232 when each manifold block is in the first position such that an egg 14 can be released as described above.

In the illustrated embodiment, a pneumatically-operated piston 52, which serves as means for moving each respective manifold block 232 from the first position to the second position, is positioned above each manifold block upper surface 232a. Each piston 52, when activated via a respective pneumatic cylinder 54, is configured to apply a downwardly directed force to the upper surface 232a of a respective manifold block 232 so as to move the manifold block 232 downward towards an egg 14 so that the egg can be engaged by a flexible cup 48 as described above. It is understood that the present invention is not limited to the illustrated embodiment. Furthermore, it is understood that each piston 52 may be actuated in various ways, including but not limited to, mechanical actuators, hydraulic actuators, and electrical actuators.

It is understood that the present invention is not limited to the illustrated manifold block 232. Various configurations may be utilized without departing from the spirit and intent of the present invention. For example, various types of pipe/tubing connectors and/or fittings known to those of skill in the art can be utilized to perform the function of the manifold block 232.

The illustrated egg removal apparatus 230 also includes a source or supply of pressurized air 140, which is configured to maintain a substantially constant air pressure. A set of air lines 142 extend from the pressurized air supply 140. Each of the air lines preferably includes a nozzle 144 that is positioned adjacent a respective egg 14 retained in seated relation with a respective flexible cup 48. Preferably, each nozzle 144 is positioned between about one-quarter inch (0.25") and about three inches (3.0") from a respective egg 14 and indicated as D in FIG. 20.

In the illustrated embodiment, each nozzle 144 has an end portion 144a with a generally straight configuration. However, it is to be understood that the nozzles 144 may each have end portions 144a with various configurations, such as a diverging configuration. Exemplary nozzles 144 include 1009SS ⅛" NPT stainless steel adjustable nozzles from EXAIR, Inc., 1250 Century Circle North, Cincinnati, Ohio.

As illustrated in FIG. 20, each nozzle 144 may be oriented along a direction that is substantially transverse to the horizontal direction 131 of the moving egg flat 10. However, each nozzle 144 may also be oriented along a direction that is substantially parallel with the horizontal direction 131 of the moving egg flat 10. Each air line 142 also preferably includes a valve 146 located between a respective nozzle 144 and the air supply 140. Each valve 146 serves as means for controlling a stream of air from the pressurized air supply 140 through a nozzle 144 for a predetermined period of time. Each valve 146 is preferably an electrically actuated valve.

Operational steps of the illustrated embodiment of FIGS. 20 and 21 are similar to those described above with respect to FIGS. 14–19. An egg flat 10 containing a plurality of eggs 14 continuously moving along a horizontal direction 131 such that when a flexible cup 48 is positioned above egg 14e the manifold block 232 is moved downwardly via actuator 52 so that the flexible cup 48 contacts the egg 14e while the internal passageway 235 is under vacuum. Accordingly, as described above, vacuum is provided into the flexible cup 48 to maintain the egg 14e in seated relation therewith.

As illustrated in FIG. 21, the manifold block 232 is moved upwardly towards the first position in the direction of (i.e., towards) the actuator. Vacuum within the flexible cup 48 is destroyed (as described above) and the egg 14e is released from the flexible cup 48. At about the same time that the egg 14e is released from the flexible cup 48, a horizontal stream of air is applied to the egg 14e to propel the egg 14e into the receptacle 133. Preferably, a stream of air has a duration of between about 50 milliseconds and about 300 milliseconds.

Figure 22:
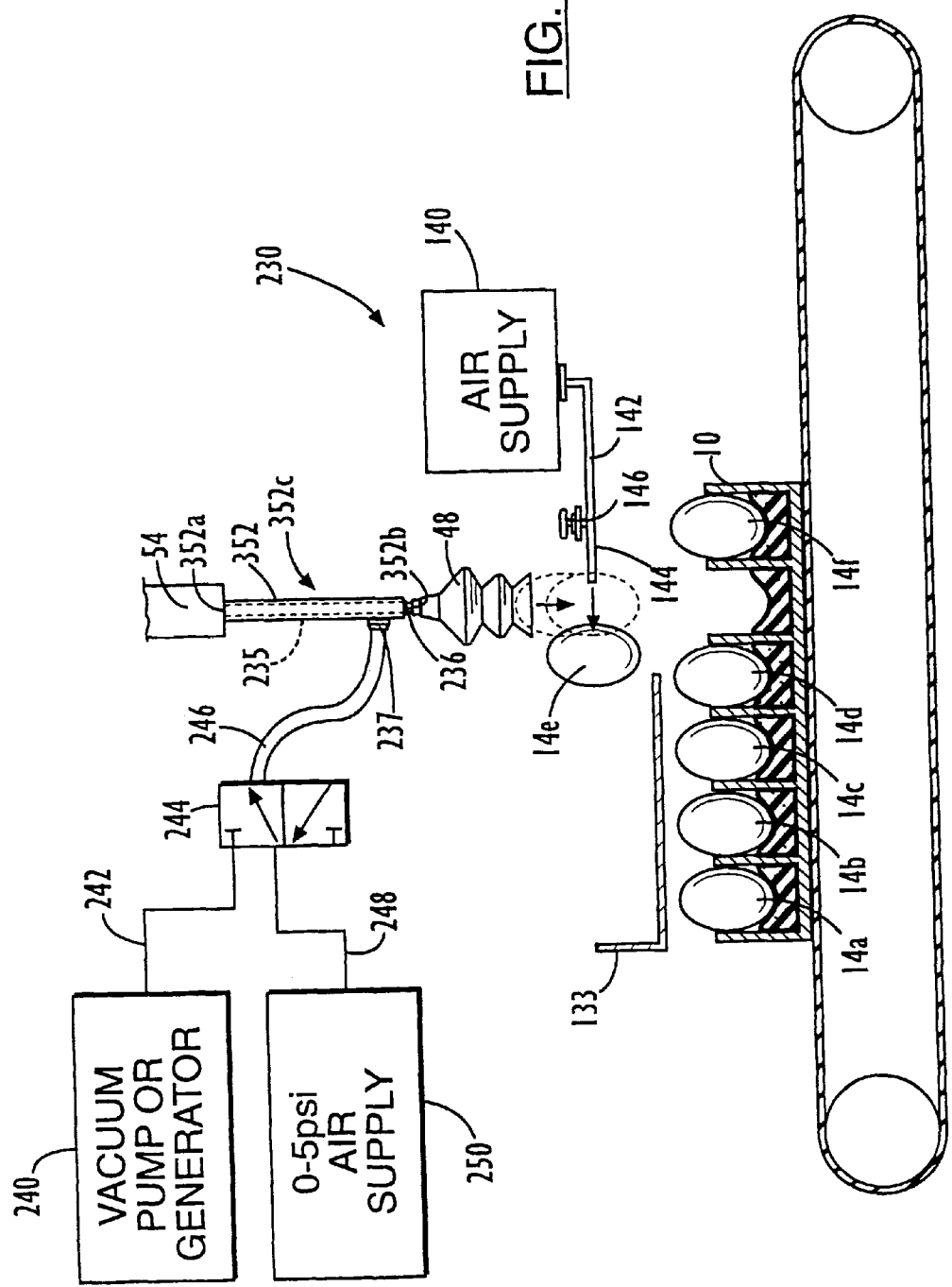
FIG. 22 is a side elevation view of an egg removal apparatus according to another embodiment of the present invention.

Referring now to FIG. 22, another embodiment of the present invention is illustrated. In this embodiment, an apparatus 230 for removing eggs 14 from an egg flat 10 that is moving in a substantially horizontal direction (indicated by arrow 131) includes a plurality of actuators 352, each positioned above a respective egg 14 in the egg flat 10 and each supported for reciprocal movement between first and second positions. Each actuator 352 may be a pneumatically-operated piston as described above.

A receptacle 133 is positioned above the egg flat 10 and adjacent the actuators 352, as illustrated. Each illustrated actuator 352 includes opposite upper and lower end portions 352a, 352b and an internal passageway 235 that terminates at a first nozzle 236 extending from the lower end portion 352b.

A flexible cup 48 is secured to the first nozzle 236 extending from each actuator 352, as illustrated. Each flexible cup 48 is in communication with the internal passageway 235 within a respective actuator 352. Accordingly, positive air pressure can be provided to each flexible cup 48 via the internal passageway 235 and vacuum can be provided to each flexible cup 48 via the internal passageway 235 as described above. In the illustrated embodiment, vacuum and positive air pressure is provided into the internal passageway 235 via a second nozzle 237 that extends from an intermediate portion 352c of the actuator 352.

Operational steps of the illustrated embodiment of FIG. 22 are similar to those described above with respect to FIGS. 14–19.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An apparatus for removing eggs from an egg flat, comprising:

a plurality of flexible cups, wherein each flexible cup is positioned above a respective egg in the egg flat, wherein each flexible cup is supported for reciprocal movement between first and second positions, wherein each flexible cup is configured to engage and retain an egg in seated relation therewith when moved to the second position and vacuum is provided within the flexible cup, and wherein each flexible cup is configured to release a respective egg when moved to the first position and vacuum within the flexible cup is destroyed;

a receptacle positioned above the egg flat; and means for applying a stream of air to each egg retained in seated relation with a respective flexible cup when in the first position to thereby propel each respective egg into the receptacle.

2. An apparatus according to claim 1 wherein the means for applying a stream of air to each egg retained in seated relation with a respective flexible cup comprises means for applying a stream of air at an angle transverse to a horizontal direction.

3. An apparatus according to claim 2 wherein the means for applying a stream of air to each egg retained in seated relation with a respective flexible cup comprises:

a supply of pressurized air;

a plurality of air lines in fluid communication with the pressurized air supply, wherein each of the plurality of air lines includes a nozzle positioned adjacent a respective egg retained in seated relation with a respective flexible cup; and means for providing a stream of air from the pressurized air supply through each of the nozzles for a predetermined period of time.

4. An apparatus according to claim 3 wherein the predetermined period of time is between about 50 milliseconds and about 300 milliseconds.

5. An apparatus according to claim 3 further comprising means for maintaining each stream of air at a pressure that is substantially constant.

6. An apparatus according to claim 3 wherein each nozzle is positioned between about 0.5 inches and about 3.0 inches from a respective egg.

7. An apparatus according to claim 1 further comprising means for moving each flexible cup from the first position to the second position.

8. An apparatus according to claim 1 further comprising means for creating a vacuum within each respective flexible cup.

9. An apparatus according to claim 1 further comprising means for automatically returning a respective flexible cup from the second position to the first position.

10. An apparatus according to claim 1 further comprising means for destroying vacuum within a flexible cup to facilitate releasing an egg held in seated relation therewith.

11. An apparatus according to claim 1 further comprising means for selecting an egg to be removed from the egg flat.

12. An apparatus for removing eggs from an egg flat that is moving along a substantially horizontal direction, comprising:

a frame positioned above the egg flat;

a receptacle positioned above the egg flat and adjacent the frame;

a manifold removably secured to the frame, the manifold comprising opposite upper and lower surfaces, a plurality of internal passageways, and a plurality of plunger bores extending from the upper surface to the lower surface, wherein each plunger bore is in communication with one of the internal passageways;

a plurality of elongated plungers, each having opposite first and second ends and an axially-extending internal bore that terminates at a first port in the plunger first end and at an opposite second port in a medial portion of the plunger between the first and second ends, wherein each plunger is supported for reciprocal movement between first and second positions in a respective plunger bore, and wherein the plunger second port is in communication with a manifold internal passageway when the plunger is moved to the second position;

a plurality of flexible cups, each secured to a respective plunger first end and each in communication with an internal bore of the respective plunger, wherein each flexible cup is configured to engage and retain an egg in seated relation therewith when a plunger secured thereto is moved to the second position so that vacuum can be provided within the flexible cup via the plunger internal bore and wherein each flexible cup is configured to release a respective egg when a plunger secured thereto is moved to the first position; and means for applying a stream of air to each egg retained in seated relation with a respective flexible cup when the frame is in the first vertical location to thereby propel each respective egg into the receptacle.

13. An apparatus according to claim 12 wherein the means for applying a stream of air to each egg retained in seated relation with a respective flexible cup comprises means for applying a stream of air at an angle transverse to the horizontal direction of the moving egg flat.

14. An apparatus according to claim 13 wherein the means for applying a stream of air to each egg retained in seated relation with a respective flexible cup comprises:

a supply of pressurized air;

a plurality of air lines in fluid communication with the pressurized air supply, wherein each of the plurality of air lines includes a nozzle positioned adjacent a respective egg retained in seated relation with a respective flexible cup; and means for providing a stream of air from the pressurized air supply through each of the nozzles for a predetermined period of time.

15. An apparatus according to claim 14 wherein the predetermined period of time is between about 50 milliseconds and about 300 milliseconds.

16. An apparatus according to claim 14 wherein each nozzle is positioned between about 0.5 inches and about 3.0 inches from a respective egg.

17. An apparatus according to claim 13 further comprising means for maintaining each stream of air at a pressure that is substantially constant.

18. An apparatus according to claim 12 further comprising means for moving each plunger from the first position to the second position.

19. An apparatus according to claim 18 further comprising means for automatically returning a respective plunger from the second position to the first position upon removal of the downwardly directed force.

20. An apparatus according to claim 12 further comprising means for creating a vacuum within the internal passageways.

21. An apparatus according to claim 20 wherein the internal passageways terminate at an aperture in the manifold and wherein the means for creating a vacuum within the internal passageways comprises means for applying vacuum to the internal passageways via the aperture.

22. An apparatus according to claim 12 wherein the means for moving a respective plunger from the first position to the second position comprises means for applying a downwardly directed force to the plunger second end so as to move the plunger downward within a respective plunger bore.

23. An apparatus according to claim 12 further comprising means for destroying vacuum within a flexible cup to facilitate releasing an egg held in seated relation therewith.

24. An apparatus according to claim 12 further comprising means for selecting an egg to be removed from the egg flat.

* * * * *